(12) United States Patent
Langen

(10) Patent No.: US 8,002,722 B2
(45) Date of Patent: Aug. 23, 2011

(54) SYSTEM FOR PRODUCING AN ORTHOPEDIC SPLINT

(75) Inventor: Günter Langen, Wolfstein (DE)

(73) Assignee: Karl Otto Braun GmbH & Co., KG, Wolfstein (DE)

( * ) Notice: Subject to any disclaimer, the term of this patent is extended or adjusted under 35 U.S.C. 154(b) by 14 days.

(21) Appl. No.: 12/574,816

(22) Filed: Oct. 7, 2009

(65) Prior Publication Data
US 2010/0022928 A1 Jan. 28, 2010

Related U.S. Application Data

(63) Continuation of application No. PCT/EP2008/002770, filed on Apr. 8, 2008.

(51) Int. Cl.
*A61F 5/00* (2006.01)
(52) U.S. Cl. ............ 602/5; 602/7
(58) Field of Classification Search ........ 602/4–8, 602/20–30, 60–64; 128/878–880, 882
See application file for complete search history.

(56) References Cited

U.S. PATENT DOCUMENTS

| | | | |
|---|---|---|---|
| 3,711,866 A * | 1/1973 | Vorberg | 112/470.13 |
| 4,226,230 A | 10/1980 | Potts | |
| 4,454,873 A | 6/1984 | Laufenberg | |
| 5,003,970 A * | 4/1991 | Parker et al. | 602/50 |
| 5,520,621 A | 5/1996 | Edenbaum | |
| 5,607,387 A * | 3/1997 | Martin et al. | 602/6 |
| 6,443,919 B1 * | 9/2002 | Castro | 602/27 |
| 2004/0024337 A1 | 2/2004 | Tseng | |
| 2006/0009721 A1 * | 1/2006 | Evans | 602/5 |

FOREIGN PATENT DOCUMENTS

| | | |
|---|---|---|
| AT | 45676 | 9/1989 |
| DE | 3729262 | 3/1989 |
| DE | 19907043 | 3/2005 |
| EP | 0061642 | 10/1982 |
| EP | 0305842 | 12/1990 |
| WO | 9713479 | 4/1997 |
| WO | 02/054983 | 7/2002 |

OTHER PUBLICATIONS

DE 100 2007 017 196.1 Search Report.
PCT/EP2008/002770 Search Report.

* cited by examiner

*Primary Examiner* — Michael A. Brown
(74) *Attorney, Agent, or Firm* — Brinks Hofer Gilson & Lione

(57) ABSTRACT

The disclosure relates to a system for producing an orthopedic splint made of a cast material, wherein the system includes at least one thermoplastic cast material present as a flat material web and a template having a flat template body, wherein the cast material can be wound around the template body in a prescribed direction for generating a splint blank, and the splint blank can be activated in order to achieve deformability, particularly after cutting the cast material to length, and to a method for producing an orthopedic splint.

6 Claims, 3 Drawing Sheets

SYSTEM FOR PRODUCING AN ORTHOPEDIC SPLINT

CROSS-REFERENCE TO RELATED APPLICATIONS

Figure 1:
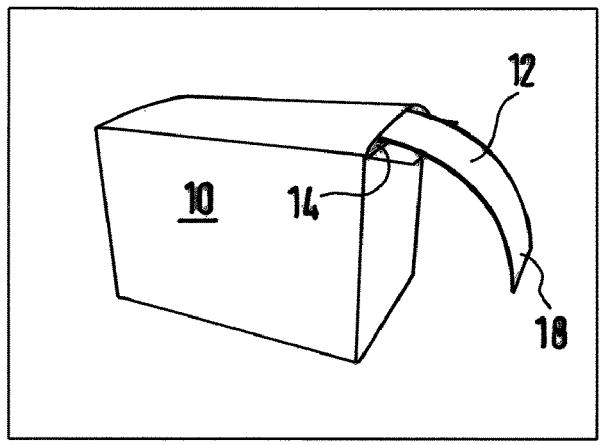

This application is a continuation of International Application No. PCT/EP2008/002770 filed on Apr. 8, 2008, which claims the benefit of DE 10 2007 017 196.1, filed Apr. 12, 2007. The disclosures of the above applications are incorporated herein by reference.

FIELD

The present disclosure relates to a system for producing an orthopedic splint.

BACKGROUND

The statements in this section merely provide background information related to the present disclosure and may not constitute prior art.

Besides the conventional cast material, alternative plastic-based dressing materials have been used for a long time. They are more advantageous than plaster casts because they have improved mechanical properties and are water-resistant, consequently washable, and owing to their rapid adjustability and hardening and low weight also ensure increased wearing comfort and improved mobility. Moreover, unlike plaster cast materials, they are X-ray permeable and thus allow X-ray examinations without having to remove the dressing. In this connection, conventional plaster cast materials as well as plastic-based dressing materials are essentially composed of an organic or inorganic textile carrier material and a plaster and/or plastic material applied thereon, whereas the plastic materials have to be differentiated between irreversibly hardening and reversibly deformable materials.

Water hardening polyurethane systems are primarily known as irreversibly hardening plastic materials, in which case the dressing materials harden within some time after being immersed in water, which allows the dressing material to be professionally applied and adapted to the person's or animal's body. As long as the plastic has not hardened, the individual layers of the dressing material may be bonded together, ultimately obtaining a dressing that consists of several layers.

With thermoplastic, reversibly deformable dressing materials like those to be used in the present disclosure, the self-adhesive properties are achieved by heating the thermoplastic plastic to or above the respective softening temperature. The material again hardens on cooling, in which case it may still be molded at temperatures below the melting point for some time. After the thermoplastic resin hardens, a dressing system with multiple layers bonded to one another is obtained.

In this case, the irreversibly hardenable polyurethane-based materials have certain disadvantages when compared to the thermoplastic materials because due to the water hardening properties, moisture-free production and complex product packaging, which make the package impervious to water and air, are required. Moreover, the corresponding resin formulations are relatively expensive and, if maximum possible moisture-free conditions are complied with, the storage stability is comparatively low. Polyurethane resins may further irritate the skin and cause noxious effects because of their isocyanate content.

An equivalent orthopedic splint as well as cast material is, for example, known from WO 02/054983. The cast material used in that case is a water hardening system, which mostly contains reactive polyurethane pre-polymers as hardenable plastic components, which irreversibly harden on contact with water. In contrast, DE 199 07 043 B4 protects a thermoplastic dressing material, which consists of a textile substrate coated with thermoplastic material, and ready-made as rolls. It may be supplied in a so called dispenser or dispensing container and be removed as quasi endless tape in the form of a flat material web.

SUMMARY

The following problems arise with thermoplastic casts used as splints: thermoplastic cast materials for splints must basically have a minimum thickness in order to ensure sufficient rigidity and stability. This minimum thickness is approx. 3 to 4 mm. An equivalent minimum thickness may in fact also be accomplished with a single-layer splint configuration, which is similar to the usual splints constructions based on glass fabric carriers, which are coated with water activated polyurethane-reactive resins. But such thick thermoplastic materials are more difficult to handle because of the high flexural rigidity that they possess in the non-activated state, compared to softer water-activating PU systems in the non-activated state, and can therefore not be provided wound into large rolls in a dispensing container. They have to be provided in the form of sheets. The sheet materials then have to be cut to numerous dimensions for the respective uses by the manufacturer, and are commercially available in this way. The disadvantage is that hospitals or practices must have a plurality of different sizes available. Moreover, when using sheets of a specified thickness, the rigidity and stability cannot be varied, nor be modified and adapted as required. There is also plenty of waste when they are adapted to relatively small limbs and joints as well as other body parts, while the sheets may probably in turn be too small for extra-long body parts.

Alternatively, a corresponding minimum thickness of about 3 to about 4 mm may also be accomplished by piling thin thermoplastic layers on top of one another, which are then substantially more flexible with regard to the single layer. Such stacks of layers may also be manufactured in prefabricated dimensions packed in boxes or cassettes depending on the body part to be treated, in which case several layers may be removed and activated in common according to the application. There still remains the problem of waste and cost effectiveness as well as of the assortment that has to be kept in order to be able to cover all possible applications. Moreover, the corresponding stacks require punching or cutting steps, and handling several layers is awkward and uncomfortable.

Based on this state of the art, the present disclosure provides a system for producing an orthopedic splint made of a cast material with at least one thermoplastic cast material available as a flat material web, in which the cast material may be ready-made as rolls in a dispenser box, and the preparation of a splint blank having the required minimum thickness is easy to produce for the user.

This is attained by a system for producing an orthopedic splint from a cast material, where the system at least includes a thermoplastic cast material available as a flat material web as well as a template with a flat template body, where the cast material is wound around the template body in a prescribed direction to prepare a splint blank, and the splint blank is activated for achieving deformability, in particular, if necessary, after cutting the cast material to a desired length.

The disclosure includes a method for producing an orthopedic splint according to the following steps:

a) winding a specified number of turns of a thermoplastic cast material available as a flat material web around a template body of a template in a prescribed direction;

b) fixing an external free end of the cast material to form a splint blank;

c) activation of the splint blank to achieve plastic deformability; and d) application as well as adaptation to a limb or body and/or a joint.

The producibility of a corresponding splint is considerably simplified by means of the present disclosure. The template, which may be formed by a flat template body, is used as a winding core, whereas in one form the cast material may be pulled out of a dispenser box as a first step, the cast material being available as a quasi endless flat material web. Corresponding cast material, which is available in the form of rolls of a defined geometry, has a roll diameter of approx. 20 to approx. 50 cm and a width of approx. 8 to approx. 12 cm. In this case, the width may be specified as a standard width.

Unlike splint materials based on reactive water hardening polyurethane resins, which require an hermetically sealed (water vapor impermeable) packaging film as primary packaging wrapping to prevent premature hardening due to ambient humidity, in the case of thermoplastic cast material rolls the non-activated cast material may be stored without water vapor impermeable wrapping in a standard cardboard box. The storage stability is considerably improved, since the thermoplastic material does not harden prematurely and may be stored at low temperatures (below 0° C.) as well as at high temperatures (up to 55° C.) for several years.

The person preparing the splint first selects a template, which, with regard to length and/or width, on the one hand corresponds to the width of the cast material, and on the other hand to the length of the limb and/or body part or joint to be treated, so that the future splint is sufficiently long. In this case, if necessary, the template may also be adapted to the body part to be treated with regard to the shape. The cast material is then wound around the template, which serves as a winding core, in the required number of layers, in which case one complete turn around the template corresponds to two layers in the splint to be produced.

Depending on the length of the flat material web, the cast material may be cut to length prior to fixing an external free end.

The cast material may be wound comparatively loose as long as the material has such retraction force that it attaches and adapts to the template on subsequent activation.

In one form the layers are wound in a manner that the longitudinal edges of the cast material lie flush on top of one another. After winding the desired number of turns, and consequently the desired number of layers, around the template for the future splint, the flat material web is then cut to length so that the same number of layers are provided on each side of the template, and the flat material web ends in the longitudinal direction with a transverse edge of the template. In this way, an equally strong bandage is accomplished and constant stability is accordingly given in all areas along the length of the splint.

If desired, it may, however, be provided that the beginning and end of the cast material, i.e. of the flat material web, are not started with a transverse edge of the template, but winding is started lengthwise in a desired prescribed position of the template so that the splint has different stabilities along its length because the number of layers is not the same all over it.

It may then be provided that the free end of the cast material, which is not within the turns of the cast material, is fastened, for example, with a clamp to the template. The rest of the cast material may, for example, remain in the storage container, i.e. in particular in the dispensing container.

The splint blank formed in this way is then activated together with the template or after being separated from the template to make it deformable. A thermoplastic cast material as in the present case is activated by heating, for example in a water bath or by means of a hot air oven, as a result of which the thermoplastic cast material is conveyed into a plastic and thus moldable state.

It may now be provided that before the activated splint blank is applied to a limb and/or body or a joint and adapted to it, the template is previously removed. Alternatively, it may, however be provided, depending on the material of the template, that the template is applied together with the splint blank and adapted to the patient. In this connection, the patients may be humans as well as animals. Hardening takes place after application and adaptation, in which case it may be provided that the splint is fastened to the patient by means of adequate fixation means, for example a bandage, providing the desired supporting effect after cooling and setting to a solid splint with good layer bonding.

It may further be provided that with this system as well as with the method multi-layer thermoplastic splints may be prepared individually for the each patient with the respectively required and/or desired supporting effect and consequent stability and rigidity, whereas the shape and length of the splint can be freely selected by choosing the corresponding template. The stability may be adjusted via the number of layers and consequently via the number of turns around the template. In this way, tedious cutting and stacking of individual layers on top of one another, as has been necessary with the longuettes, is dispensed with. Moreover, it is also not necessary to have available a large number of ready-made longuette sizes, which take up storing space. In this way, it is possible to increase the efficiency for the user and patients by means of the template provided in the system, and, apart from the variable rigidity, the assortment may be configured in a more cost effective manner.

The template is removed by simply stripping down the activated splint blank after removing, if provided, the fixation of the free end of the cast material. The clamp or equivalent to fix the free end may be integrated in the system and be stored together with the template. The corresponding fixing means, like a clamp, may in particular be fastened to the template during storing so that the template and clamp are always at hand together.

If a template is mentioned in connection with the present disclosure, at least one template is meant. A system may in particular also comprise two, three, four or a plurality of templates, in which case each template is different from all other templates in at least one dimension. A set according to the present disclosure may in particular comprise a set of templates for a limb, e.g., a forearm or lower leg, each template of the set being at least different in one dimension from the remaining templates of the set.

In addition, it may be provided that the template is in particular adjustable lengthwise and widthwise. The lengthwise adjustability, but also the widthwise adjustability may either be accomplished in the form of a telescopable splint or according to the pull-out principle, as is provided in a sliding caliper. In this way, it is possible to work with only one template, so that different templates for different applications and patients need not be provided. Individual and, if necessary, even continuous adjustability may be provided in this case so that individual adaptation to the length of each patient's limb is possible. But adjustment at discrete stages is also possible. The adjustability in width is especially advantageous when cast materials of different widths, like, for example, the standard widths of about 8, about 10, about 12.5 and about 20 cm, have to be processed. It is, however, also possible to work with templates, which are wider or narrower than the width of the flat material web.

It is thus also possible to prevent that the wrong template is at hand because it is too long for the application, which either results in that the template is possibly not used, or, for example, is shortened anyway, which is disadvantageous for applications at a later time.

If the template is provided to be adjustable in length, the user may, e.g. get the exact measure of a patient's forearm and use the template as a winding core for using the splint blank. A six-layered custom-made cast splint may, for example, thus be prepared with a few turns within a short time. Only one cut is subsequently necessary when the cast material is separated from the quasi endless material in the dispenser after winding.

In this case, the template may consist of wood, cork or also metal or ceramic material as well as of glass, plastic or a composite material. Moreover, the template may be mounted with different materials like rods, wires, straps, whereas several elements may be combined with one another. Depending on the material and contingent on whether the template should also be applied and remain in the finished splint, the template material may be selected such that it is used for further stabilizing the splint. In this case, it is necessary to prepare several templates together with the cast material because they have to be considered as disposable material. If the template is reusable, the durability of the template material is of relevance.

The shape of the template may be adapted to the anticipated use of the splint, and rectangular, but also trapezoidal or rounded as well as serrated templates may especially be prepared.

It may also be provided that the template covers the whole area, i.e. is prepared as a sheet material. Perforated or punched as well as latticed forms of the template are also possible.

Furthermore, it may also be provided that the template has one or two lateral stops. Two lateral stops may in particular be used together with the adjustability in width, as in this case only one template will also be required for rolls of the cast material available in different widths. Providing at least one lateral stop has the advantage that flush winding of the longitudinal edges of the flat material web on top of one another may be accomplished in an especially easy manner.

According to a further form, it may be provided that the template is formed by a dispensing container. This means that in this case the cast material is wound around the dispensing container, cut off and removed from the cardboard.

It may further also be provided that the template is firmly or detachably connected to the dispensing container, which consists of cardboard. The templates may be, however, supplied as separate elements, which are contained together or in particular in one dispensing container, and thus are supplied together with the latter to the user.

Winding around the template may be accomplished manually, but also by means of a holding or turning device, which may in particular contain a crank handle.

Moreover, it may be provided that before applying the splint blank to a patient transversely to its length, in particular along the place that is limited by both free end of the cast material, it is cut open and thus unfolded to a flat element. A double-length three-layered splint blank may, for example, be prepared in this way from a six-layered ring-shaped body by means of a simple cut. Something similar is especially interesting in the veterinary field when using long splints on animal legs, like horse legs for example, because winding around an only half as long template, which consequently, however, has higher stability and better manageability, and subsequent opening the winding body to form a flat material, which is half as thick, but twice as long, may significantly facilitate the accomplishment of such splint blanks.

Finally, the present disclosure includes a method for producing an orthopedic splint by means of the above mentioned steps, whereby such method has the advantage that a splint may be prepared in an especially easy and fast manner.

According to the present disclosure, it may further be provided that before step a), namely winding around the template body, the length of the template is adapted to a patient and to the part of the body to be treated. An assortment of the suitable templates may also be preconfigured.

It may likewise be provided to remove the template before application as well as adaptation to a limb.

The cast material may in this case be activated in a water bath or also in an oven.

During activation in the water bath, the whole splint blank including the template are immersed in the water bath. Even activation of a template wrapped with six layers in a water bath at a temperature of about 70° C. to about 95° C. is completed in approx. 30 to approx. 60 seconds. Owing to its retraction force, the thermoplastic cast material optimally adapts to the shape of the template, but may also be easily deformed and thus be removed from the template because it has become plastic due to the heat. Subsequently, the layers are pressed together in order to achieve a better connection of the layer bonding, and the splint blank is then adapted to the part of the body to be treated.

The thermoplastic material used for the system as well as for the method may in particular be one that has a thermoplastic plastic applied on a textile web, where a second textile web may be applied onto the thermoplastic plastic. The advantage accomplished by means of the second textile web is that it may be better unwound even after having strongly squeezed out the residual water after heating in the water bath, whereas the second textile web has no negative effect on the adherence of the layers in the finished splint material. Moreover, the second textile web contributes to the stability and improvement of the air permeability.

In this connection, it may be provided that the first and/or second textile web has an elastic configuration. The thermoplastic plastic in this case has a melting point from about 55° C. to about 90° C., and is rigid or marginally flexible at temperatures of about 50° C. or below, but not substantially softened and self-adhesive in the plastic state.

Nonwoven webs may in this case be used for the textile webs, but also scrims or knitted fabrics, woven fabrics or interlaced yarns. For example, a knitted strap with an open-pored structure may be provided.

The term "elastic" in this case includes inelastic as well as elastic malleability.

The textile webs may in this case include synthetic, regenerated and natural fibers as well as of mixtures, in which case, mixtures of elastic and inelastic fibers and/or filaments may likewise be used. In this connection, textile webs made of synthetic filaments and/or fibers of one or several synthetic materials, e.g. polyester or polyamide as inelastic yarns, and polyurethane filaments and/or fibers as elastic yarns.

The malleability may in this case be longitudinal as well as transverse, and is between about 30 and about 200% for the longitudinal malleability, further between about 60 and about 110% and further between about 85 and about 100%. The transverse malleability may be between about 10 and about 120%, further between about 30 and about 100% and between about 40 and about 90%. The malleability is in this case determined according to the method described in DIN 61632.

Such cast materials may mostly be white, whereas the color of the textile web is decisive. It is, however, also possible to use dyed textile webs.

A hydrolysis-stable, storage-stable hot melt adhesive may be used as thermoplastic plastic that melts at temperatures between about 55° C. and 90° C., between about 60° C. and about 80° C., and between about 60° C. and about 70° C., and remains plastic for some time after cooling below the melting point. In order to be suitable for use in a thermoplastic dressing material under normal conditions of use the thermoplastic plastic should resist temperatures up to about 50° C., or up to about 55° C., which means that it should not substantially soften or even decompose at these temperatures.

The hardening time after heating to or above the melting point depends on the achieved temperature and cooling speed, and in general takes between about 1 and about 15 min, or between about 2 and about 10 min, or between about 3 and about 8 min.

Suitable thermoplastic plastics having the above mentioned properties are, for example polyester, polyurethane, polyvinyl acetate or also other plastics, like, for example, linear saturated polyester combinations, like the commercially available polycaprolactone CAPA R 640 (manufacturer: SOLVAY-INTEROX, Warrington, GB, a granulated polycaprolactone with a melting point of about 57° C.). An example of a suitable thermoplastic polyurethane is the commercial product UNEX 4103 (manufacturer: DAKOTA COATINGS, Neerhonderd, Belgium). Mixtures of different thermoplastic plastics may, however, also be used; besides, auxiliary substances or additives may be added. Thermoplastic plastics, which in the rigid state have a certain residual flexibility, instead of completely hardening, may also be used. Examples of this are ethylene-acrylic acid copolymers, ethylvinyl acetate copolymers and polyurethanes. By using such dressing materials, the body part treated with the prepared dressing is not fully immobilized, but only semi-rigid stabilization is accomplished, which make functional load of the involved body parts possible.

An equivalent thermoplastic cast material may be produced according to DE 199 07 043 B4.

Further areas of applicability will become apparent from the description provided herein. It should be understood that the description and specific examples are intended for purposes of illustration only and are not intended to limit the scope of the present disclosure.

DRAWINGS

Figure 2:
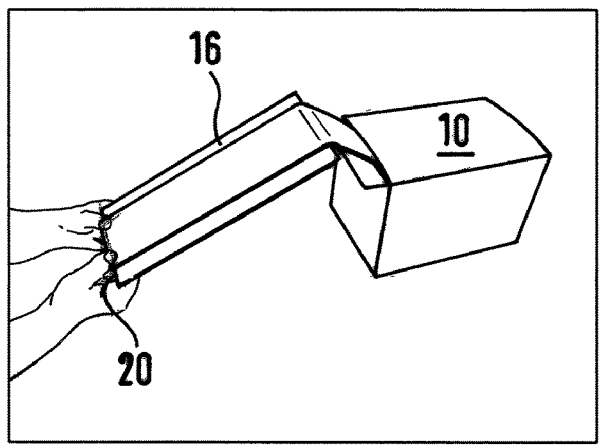
Figure 3:
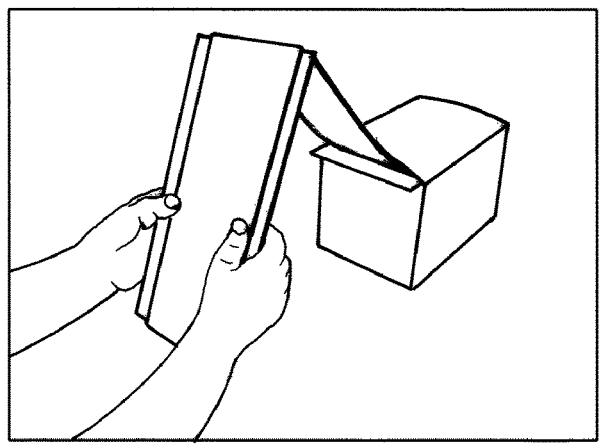
Figure 4:
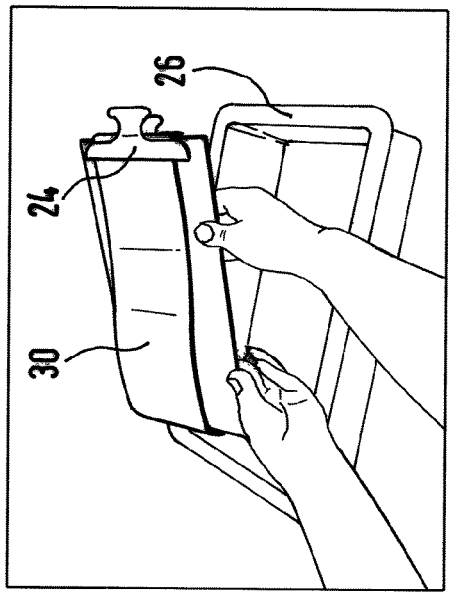
Figure 6:
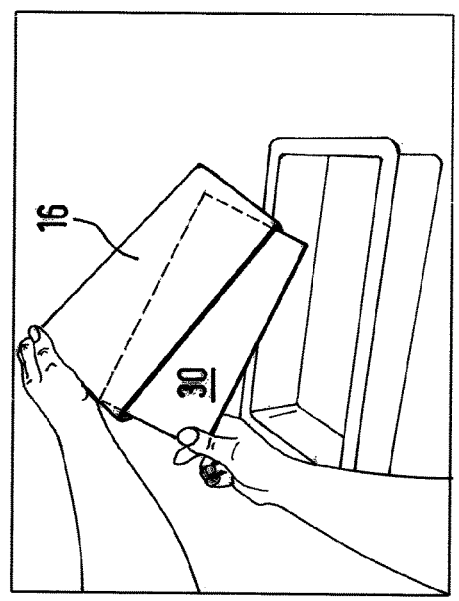
Figure 5:
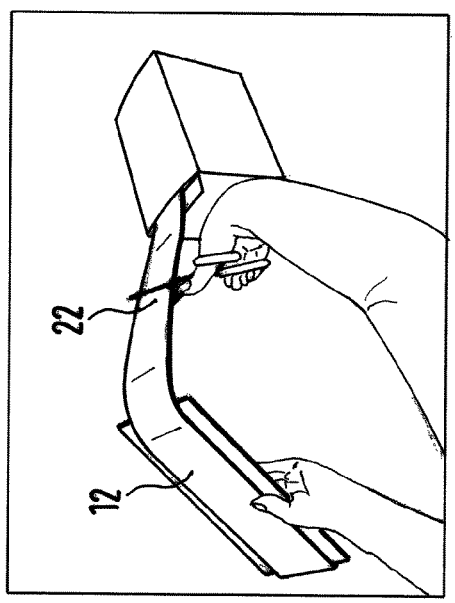
Figure 7:
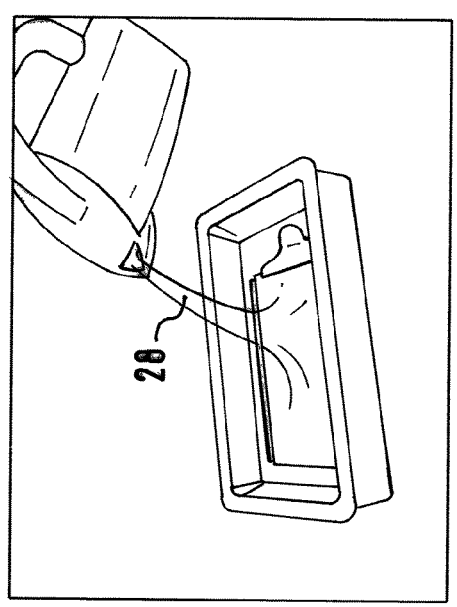
Figure 8:
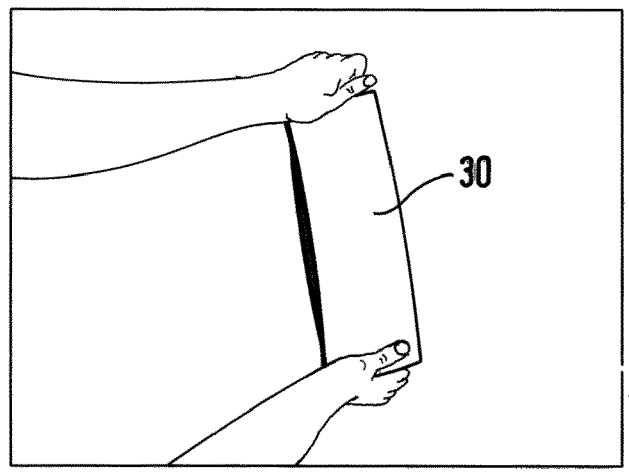
Figure 9:
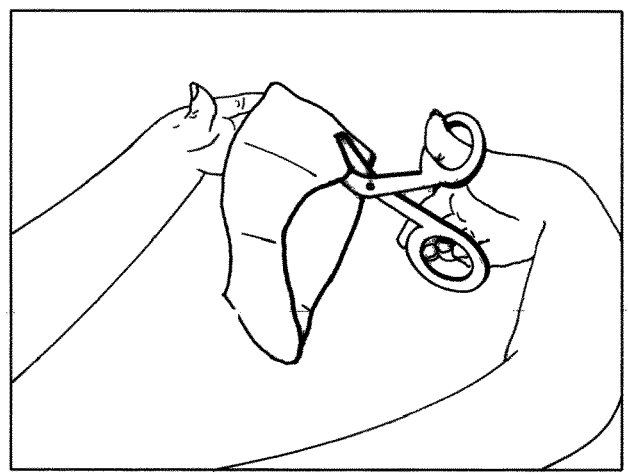
Figure 10:
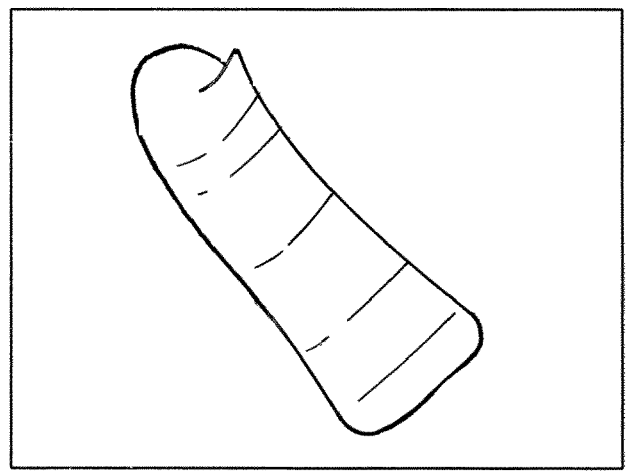

In order that the disclosure may be well understood, there will now be described various forms thereof, given by way of example, reference being made to the accompanying drawings, in which:

FIG. 1 shows a dispensing container opened for use;
FIG. 2 shows a winding procedure;
FIG. 3 shows a start of the wrapping;
FIG. 4 shows a splint;
FIG. 5 shows a free end clamped by a clamping means;
FIG. 6 shows a blank placed in an activating device;
FIG. 7 shows a template being removed from out of a splint blank;
FIG. 8 shows a finished splint blank;
FIG. 9 shows a splint blank smoothed out, squeezed, and flattened; and
FIG. 10 shows a finished splint.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

In this connection, FIGS. 1 to 10 show the procedure for producing an orthopedic splint with a system according to the present disclosure as well as according to the disclosed method.

FIG. 1 shows a dispensing container 10, in which a cast material based on a thermoplastic plastic 12 is contained as a quasi endless roll consisting of a flat material web. The box is opened for use and a free end 18 of the cast material is pulled out through a dispensing opening 14 so that is may grabbed by the user.

For the production of an orthopedic or medical splint, the person to be treated or animal to be treated are first measured, and a winding template 16 of the desired width adjusted to the width of the cast material 12 as well as adjusted to the length of the limb to be treated with the splint is selected. The free end 18 of the thermoplastic cast material is applied to a transverse edge 20 of the template 16, where it is fastened. The cast material is then wound around the template 16 while it is pulled out of the container 10. Each 360° turn around the template 16 in this case results in two layers for a future splint. FIG. 3 shows the winding procedure, while FIG. 2 shows the start of the wrapping. The desired number of layers is achieved by continuously turning the template 16, in which case it is provided that, with regard to their longitudinal edges, the individual layers lie flush on top of one another.

After, for example, four turns of the template 16 an eight-layered splint blank is provided, as shown in FIG. 4.

The cast material 12 may then be cut to length by means of a simple cut, while the cutting to length procedure is performed such that the free end 22 of the cast material, which is formed by cutting to length, in turn ends flush with the transverse edge 20 or the other transverse edge of the template 16. The free end 22 is then clamped by means of a fixing means, in this case a clamp 24, to the template 16 (FIG. 5). Alternatively, however, the free end 22, but also the start of the cast material may not end flush with a transverse edge of the template 16. The splint blank created in this way is then placed into an activating device, for example a water bath, whereas the water bath is in this case indicated by a container 26, into which correspondingly heated water 28 is filled (FIG. 6). Depending on the number of layers and with complete immersion of the splint blank, which in its entirety is designated with the reference numeral 30, activation by heating the thermoplastic plastic is achieved after a retention time of 30 to 60 seconds. The splint blank 30 may then be removed from the water bath, and the template 16 is pulled out of the splint blank 30 and removed in this way, as shown in FIG. 7. FIG. 8 shows the finished splint blank 30, which is now warmed and at the same time plastically deformable. According to FIG. 8, the splint blank 30 is now smoothened out, squeezed and flattened in order to remover excessive water and achieve good layer bonding.

FIG. 9 shows an optional configuration, in which the winding body, which is formed by the splint blank 30, is cut in two at one point in the transverse direction, so that a splint blank with half the number of layers but double length is obtained. Something similar may in particular be advantageous for veterinary applications.

FIG. 10 shows the finished splint, where the splint blank according to FIG. 8 was applied onto a limb to be treated and stabilized, and in this case was adapted and fixed at the desired place and in the desired position by means of a bandage, for example, until the splint blank has hardened to the finished splint 40. Subsequently, the splint 40 may be applied to a patient's limb or joint in the desired way and is used to stabilize it.

It should be noted that the disclosure is not limited to the various forms described and illustrated as examples. A large variety of modifications have been described and more are within the scope of the present disclosure. These and further modifications as well as any replacement by technical equivalents may be added to the description and figures, without leaving the scope of the protection of the disclosure and of the present patent.

What is claimed is:

1. A method for producing an orthopedic splint according to the following steps:
    a) winding a thermoplastic cast material, which is available as a flat material web, around a template body of a template in a prescribed direction with a specified number of turns;
    b) fixing an external free end of the cast material to form a splint blank;
    c) activating the splint blank to accomplish plastic deformability, and
    d) applying and adaptating the splint blank to at least one of a limb or body.

2. The method according to claim 1, wherein the template is at least one of selected and adapted with regard to at least one of its length and width prior to step a).

3. The method according to claim 1, wherein the template is removed prior to step d).

4. The method according to claim 1, wherein the cast material is cut to length prior to fixing the external end.

5. The method according to claim 1, wherein the winding of the cast material is cut open transversely to the winding direction in order to double the length of the splint and halving the specified number of layers prior to step c).

6. The method according to claim 1, wherein the activation is carried out as heat activation.

* * * * *